United States Patent
Fine et al.

(10) Patent No.: US 10,045,730 B2
(45) Date of Patent: Aug. 14, 2018

(54) METHODS AND SYSTEMS FOR RAPID SCREENING OF MILD TRAUMATIC BRAIN INJURY

(71) Applicant: The MITRE Corporation, McLean, VA (US)

(72) Inventors: Michael S. Fine, Gaithersburg, MD (US); Matthew Shields Caywood, Washington, DC (US)

(73) Assignee: The MITRE Corporation, McLean, VA (US)

( * ) Notice: Subject to any disclaimer, the term of this patent is extended or adjusted under 35 U.S.C. 154(b) by 831 days.

(21) Appl. No.: 14/483,741

(22) Filed: Sep. 11, 2014

(65) Prior Publication Data

US 2016/0073945 A1   Mar. 17, 2016

(51) Int. Cl.
*A61B 5/00*     (2006.01)
*A61B 5/11*     (2006.01)
(Continued)

(52) U.S. Cl.
CPC ............ *A61B 5/4064* (2013.01); *A61B 3/113* (2013.01); *A61B 5/1124* (2013.01); *A61B 5/742* (2013.01);
(Continued)

(58) Field of Classification Search
CPC ....... A61B 5/11; A61B 5/1101; A61B 5/1124; A61B 5/1125; A61B 5/4064; A61B 5/742; A61B 5/6898; A61B 3/113
See application file for complete search history.

(56) References Cited

U.S. PATENT DOCUMENTS 5,241,332 A * 8/1993 Farrell ..................... A61B 5/16
                                                              351/203
5,775,332 A    7/1998 Goldman
(Continued)

FOREIGN PATENT DOCUMENTS

| WO | WO-2009/039806 | 4/2009 |
| WO | WO-2013/012739 | 1/2013 |
| WO | WO-2014/039861 | 3/2014 |

OTHER PUBLICATIONS

Halder et al. (Jan. 2007) "Electrophysiological and hemodynamic evidence for late maturation of hand power grip and force control under visual feedback," *Human Brain Mapping*, 28(1): 69-84.

(Continued)

*Primary Examiner* — Max Hindenburg
(74) *Attorney, Agent, or Firm* — Morrison & Foerster LLP

(57) ABSTRACT

The disclosure provides for easy, reliable, and rapid screening of a mild traumatic brain injury (mTBI) based on a modeling of a subject's tracking of a dynamic target during the course of a simple motor tracking task. The gathered tracking data can be used to calculate tracking errors between the subject's actual input (e.g., grip force) and the intended target input. The tracking errors may be used to generate numerical values for model parameters that correlate the subject's responses to the tracking errors during the course of the dynamic motor tracking task. A classification model may be used to compare the model values to multi-subject model values of known diagnoses for mTBI. The entire screening process can be effectively administered in a matter of minutes or less, and with a high degree of accuracy.

19 Claims, 13 Drawing Sheets

(51) Int. Cl.
*A61B 3/113* (2006.01)
*G06K 9/00* (2006.01)
*G16H 50/20* (2018.01)
G06K 9/62 (2006.01)
G06K 9/22 (2006.01)
G06K 9/32 (2006.01)

(52) U.S. Cl.
CPC ......... *G06K 9/00355* (2013.01); *G16H 50/20* (2018.01); *A61B 5/6898* (2013.01); *G06K 9/00536* (2013.01); *G06K 9/228* (2013.01); *G06K 9/3241* (2013.01); *G06K 9/6271* (2013.01); *G06K 9/6272* (2013.01); *G06K 2209/05* (2013.01)

(56) References Cited

U.S. PATENT DOCUMENTS

| | | | |
|---|---|---|---|
| 5,852,489 A * | 12/1998 | Chen | A61H 5/00 351/237 |
| 6,231,525 B1 | 5/2001 | Paske | |
| 6,517,480 B1 * | 2/2003 | Krass | A61B 5/16 600/300 |
| 6,678,549 B2 | 1/2004 | Cusimano et al. | |
| 6,896,656 B2 | 5/2005 | Krass | |
| 7,295,124 B2 | 11/2007 | Guillen | |
| 8,323,190 B2 | 12/2012 | Vitiello et al. | |
| 8,568,312 B2 | 10/2013 | Cusimano Reaston et al. | |
| 8,585,589 B1 * | 11/2013 | Cinberg | A61B 3/113 351/209 |
| 9,004,687 B2 * | 4/2015 | Stack | A61B 3/113 351/209 |
| 9,039,632 B2 * | 5/2015 | Kiderman | A61B 5/16 600/558 |
| 9,055,904 B2 * | 6/2015 | Yoo | A61B 3/0033 |
| 9,084,573 B2 * | 7/2015 | Cinberg | A61B 3/113 |
| 9,101,312 B2 * | 8/2015 | Waldorf | A61B 3/032 |
| 9,642,522 B2 * | 5/2017 | Samadani | A61B 3/113 |
| 9,717,459 B2 * | 8/2017 | Sereno | A61B 5/6898 |
| 2004/0097838 A1 | 5/2004 | Paske et al. | |
| 2010/0063944 A1 | 3/2010 | Grogan et al. | |
| 2011/0117094 A1 | 5/2011 | Strittmatter et al. | |

OTHER PUBLICATIONS

Hiemstra D. (1994). "The effects of lower limb strength training on the locomotor skills of subjects with a traumatic brain injury," *UMI Dissertations Publishing*, University of Alberta (Canada); 109 pages.

* cited by examiner

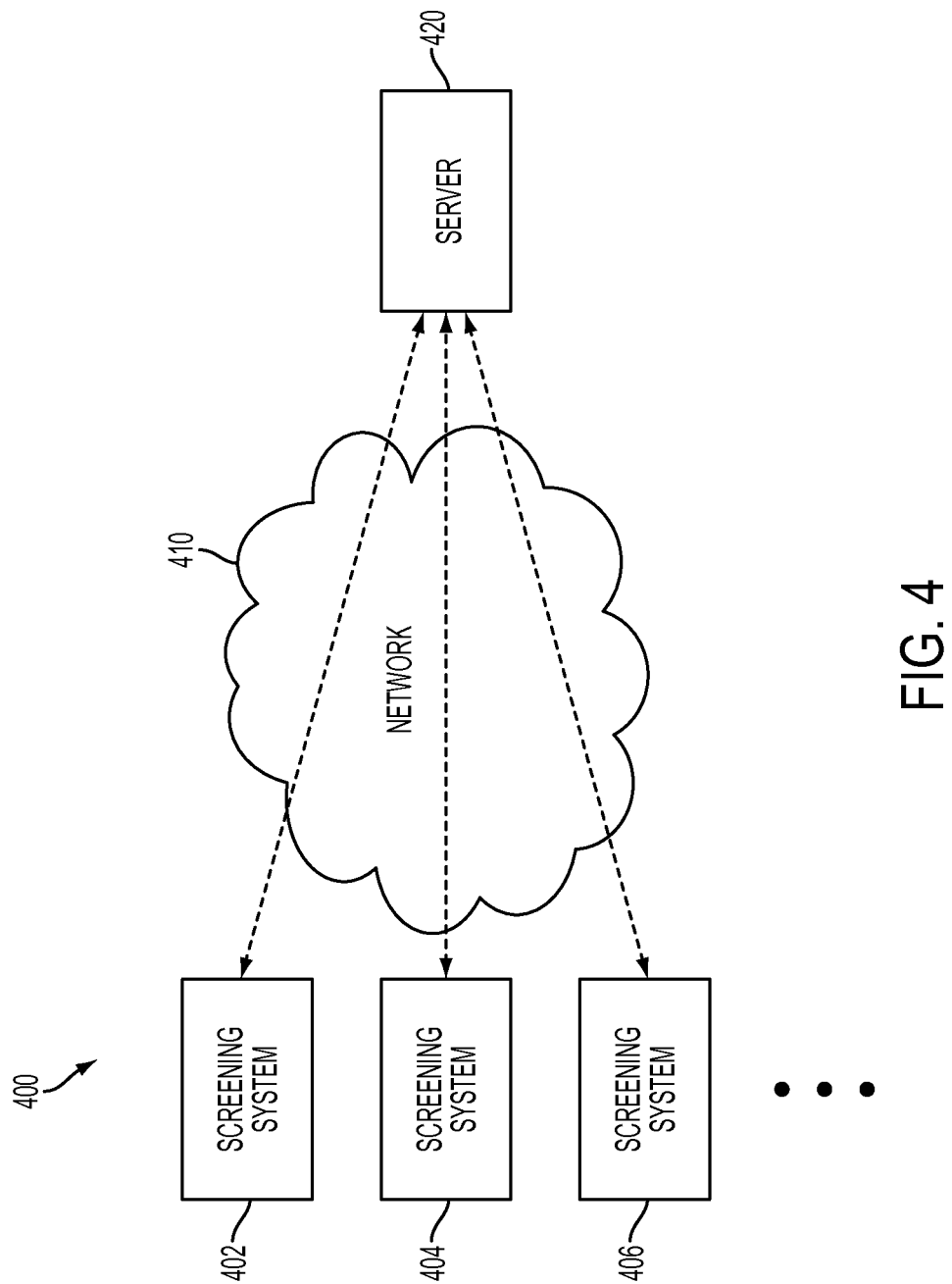

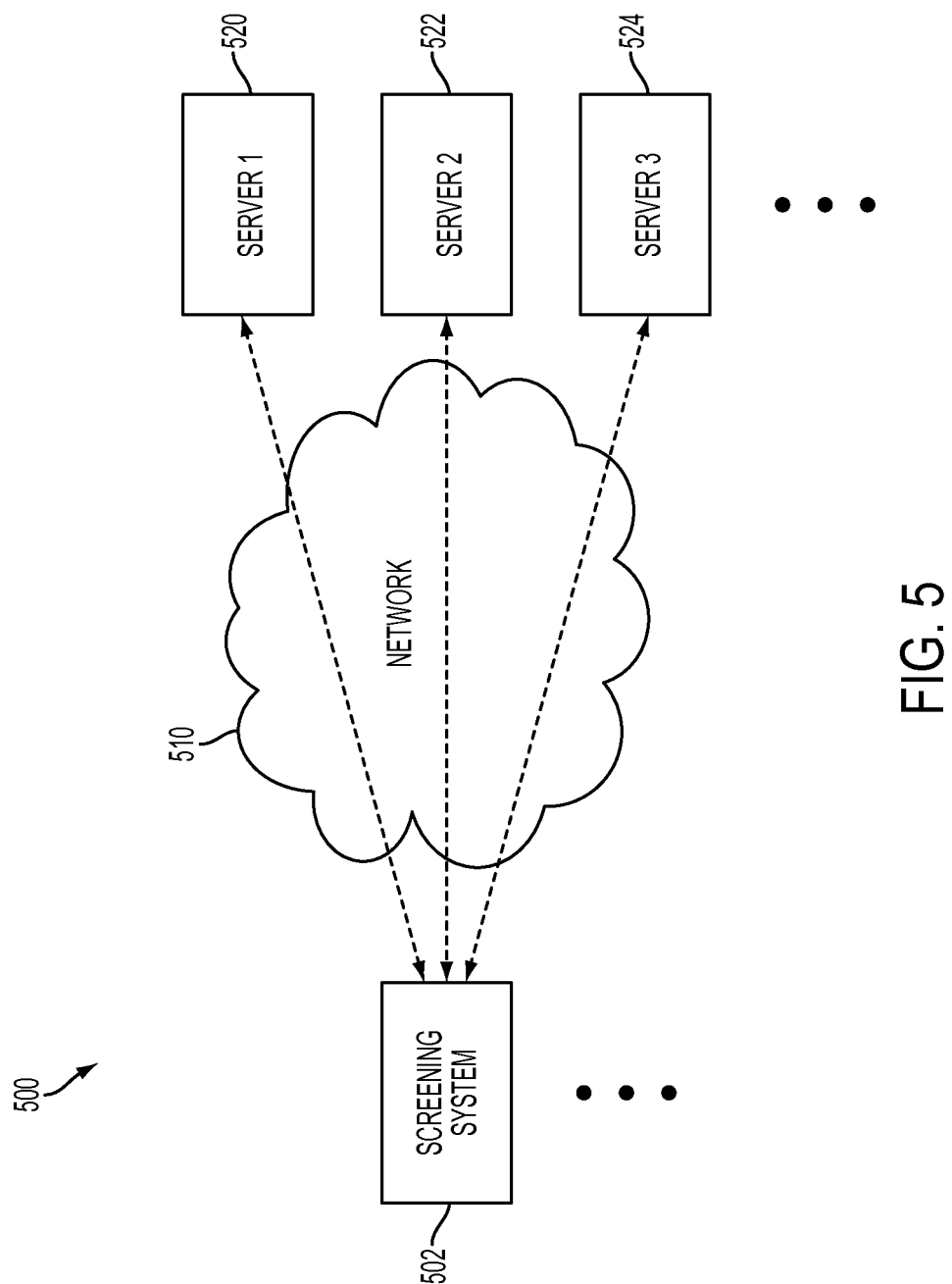

| DATA | CLASSIFICATION ACCURACY | CONFUSION MATRIX | |
|---|---|---|---|
| | | TRUE POSITIVE | FALSE POSITIVE |
| | | FALSE NEGATIVE | TRUE NEGATIVE |
| $K_p, K_d, \tau$ | 89.7% | 13 | 1 |
| | | 2 | 13 |
| MACE | 72.4% | 11 | 4 |
| | | 4 | 10 |
| PHQ-9 | 72.4% | 11 | 4 |
| | | 4 | 10 |
| TRAILS MAKING TEST A | 55.2%* | 8 | 6 |
| | | 7 | 8 |
| STDEV, $\tau$ | 69.0%* | 12 | 6 |
| | | 3 | 8 |

FIG. 12

METHODS AND SYSTEMS FOR RAPID SCREENING OF MILD TRAUMATIC BRAIN INJURY

FIELD OF THE INVENTION

The present disclosure relates generally to rapid screening for a brain injury, and more specifically to systems and methods for rapid screening for mild traumatic brain injury (mTBI) by modeling a subject's responses during the course of a dynamic motor tracking task.

BACKGROUND OF THE INVENTION

Mild traumatic brain injury (mTBI), commonly referred to as a concussion, is a type of traumatic brain injury (TBI) caused by a fall, a blow to the head, or another injury that jars or shakes the brain inside the skull. In some instances, there may be no lasting symptoms or ill effects because the brain is protected by the skull and cushioned by the cerebrospinal fluid to absorb impacts. However, the force of an impact may be beyond the ability of the skull and cerebrospinal fluid to fully protect the brain, which can lead to mTBI.

Diagnosing mTBI in its earliest and least problematic stages is critical to effective intervention, which will improve clinical outcomes and reduce costly long term care. In its Science and Technology (S&T) Path Ahead report of Oct. 3, 2012, the Army proclaims "early detection of TBI" as one of its top challenges, with planned investments of $5 million for FY14 and $40 million for FY14-18 to address the challenge. Further, many sporting leagues, from grade school and college athletics to professional leagues, have a need for thorough implementation of sideline concussion protocols that easily and reliably screen for mTBI and thus adequately protect athletes from risk of further injury. Therefore, it would be helpful, especially for entities such as the military and various sports leagues, to have a mTBI screening system that can easily and reliably screen for mTBI immediately following a traumatic exposure.

Common symptoms of mTBI include psychomotor slowing, poor concentration, and decrease in attention retrieval ability, leading to increased variability of performance and overall executive dysfunction. Executive dysfunction further causes poor regulation and control of cognitive processes, including working memory, logical reasoning, and problem solving. Problematically, the onset of mTBI is very subtle, making early identification of mTBI difficult. Indeed, one of the greatest challenges in diagnosing mTBI is that most persons with mTBI do not exhibit clearly discernible symptoms immediately following the traumatic exposure. Symptoms may not appear for days, weeks, or even months and when they do appear, they are often nonspecific. Further, persons with mTBI are more susceptible to additional, and potentially more severe, brain damage. Therefore, the ability to reliably identify mTBI early on in its course is especially important.

The military in particular has a great need to screen for mTBI among its troops. Various mTBI symptoms, including headaches, irritability, memory impairments, dulled reaction time, and insomnia, lead to decrease in performance that is particularly dangerous for troops involved in combat or in close proximity to a hostile area. Traditional approaches to assessing mTBI, such as detailed neurological evaluations, extensive cognitive testing, and imaging, impose undesirable costs and delays, and are largely impractical to implement on a battlefield. Thus, the military has a significant need to make fast and accurate neurocognitive assessments of its personnel.

Currently available screening procedures for mTBI are largely based on a use of standard questionnaires or self-reporting of the trauma or symptoms. Standard questionnaires can be administered by emergency personnel. Some example questionnaires include the Military Acute Concussion Evaluation (MACE), the Westmead Post Traumatic Amnesia Scale (PTA), and the Acute Concussion Evaluation (ACE). However, these evaluation methods are often unreliable and impractical to administer immediately after injury in the field. For example, MACE is primarily designed to be most effective when administered immediately after injury, and studies suggest that it is clinically useful within 6 hours but ineffective after 12 hours. However, administering a dense questionnaire in the battlefield immediately following a traumatic exposure is not always practical. Recently, a number of other tests have been developed to diagnose mTBI, including the Automated Neuropsychological Assessment Test (ANAM), the Immediate Post-Concussion Assessment and Cognitive Testing (ImPACT), and the King-Devick (K-D) Test. Despite these advances, however, screening and diagnosis of mTBI still largely depend on standard questionnaires and clinical observation. There is currently no gold standard or objective means to screen for and diagnose mTBI.

As disclosed in WO 2014/039861, the content of which is hereby incorporated by reference in its entirety, it is possible to measure and monitor an individual's motor performance variability immediately after injury in the field. More specifically, WO 2014/039861 discloses a method and system for assessing intra-individual response variability as manifested in a simple motor task to screen for mTBI and to potentially diagnose mTBI or other cognitive impairments.

However, the system disclosed in WO 2014/039861 fails to achieve a high degree of accuracy for its diagnosis. It implements a simple binary classifier and simple metrics that cannot diagnose mTBI with a sufficient degree of accuracy to make its use practical as a reliable mTBI screening system. Thus, the system disclosed in WO 2014/039861 alone does not negate the need for additional testing of the subject to ensure a reliable diagnosis. Therefore, it would be helpful to rapidly screen for mTBI with a high degree of accuracy to allow for its easy and reliable use in a real world setting.

SUMMARY OF THE INVENTION

The disclosed systems and methods provide for easy, reliable, and rapid screening of a mild traumatic brain injury (mTBI) based on a modeling of a subject's tracking of a dynamic target during the course of a simple motor tracking task. For example, a subject may use a handheld input device to move a graphical image rendered on a computer display to track a dynamic visual target on the display. Data is gathered, via the handheld input device, from a subject performing the motor tracking task.

In some embodiments, the gathered tracking data can be used to calculate tracking errors between the subject's actual input force, pressure, movement, and/or gesture, and the intended target force, pressure, movement, and/or gesture. The tracking errors may then be used to generate numerical values for model parameters that best correlate the subject's responses to the tracking errors during the course of the dynamic motor tracking task. The model values may in turn be compared to other numerical values for corresponding model parameters of known diagnoses to screen the subject for mTBI. In some embodiments, the model values of known diagnoses may include data from multiple subjects includes both known mTBI patients and non-mTBI controls. Thus, the subject's model values and the known multi-subject model values can be used by a classification model to diagnose for the presence of mTBI with a high degree of accuracy. The entire screening process can be effectively administered in a matter of minutes or less.

In some embodiments, a method for screening of a brain injury using one or more electronic devices includes displaying an image of a dynamic target on a display for a subject to track using a sensing component and receiving, from the sensing component, tracking data representing the subject's tracking of the dynamic target. The method also includes displaying in real time an image of a tracker on the display representing the subject's tracking of the dynamic target, determining a model value, derived from target data and the tracking data, indicative of the subject's corrective actions in response to deviations between the tracker and the dynamic target over a period of time, comparing the model value to one or more multi-subject model values, and outputting a screening indicator representing the likelihood that the subject has a brain injury based on the compared model values.

In some embodiments, the method further includes comparing the model value to a corresponding prior model value of the subject, and outputting a prior screening indicator representing a recovery progress of the subject from a brain injury based on the comparison between the model values. In some embodiments, the prior screening indicator includes a screening indicator of the subject from a threshold amount of time prior to the current time. In some embodiments, the brain injury is a mild traumatic brain injury. In some embodiments, the one or more electronic devices include one or more portable devices. In some embodiments, the dynamic target moves in accordance with one or more of multiple target modes, and each of the target modes instructs the dynamic target to move in a unique pattern. In some embodiments, the sensing component is a dynamometer that detects the subject's hand grip force. In some embodiments, the sensing component is an eye-tracking device.

In some embodiments, the tracker is an icon on the display that expands and contracts in response to the subject's input using the sensing component. In some embodiments, the model value is derived from the tracking data via a response model that correlates the deviations between the tracker and the dynamic target to the subject's corrective actions over a period of time. In some embodiments, the model value includes one or more best-fit parameters representing optimized fit values quantified by the response model using the tracking data. In some embodiments, the one or more multi-subject model values include one or more model values of previously tested subjects.

In some embodiments, the previously tested subjects include individuals known to have a brain injury and individuals known not to have a brain injury. In some embodiments, the previously tested subjects include individuals having two or more of gender, height, weight, and age group in common with the subject. In some embodiments, the previously tested subjects include individuals employed in the same field of employment as the subject. In some embodiments, comparing the model value to a multi-subject model value includes implementing a machine learning predictor that uses a Gaussian process. In some embodiments, the machine learning predictor includes at least one of a third-party assessment score of the subject and third-party assessment scores of the multi-subjects. In some embodiments, the machine learning predictor compares the subject third-party assessment score to the third-party multi-subject assessment scores. In some embodiments, the third-party assessment scores include evaluative scores from publicly available post-concussion standard questionnaires In some embodiments, outputting the screening indicator includes displaying at least one of a light in one or more colors, an audio signal or text.

In some embodiments, a system for screening of a brain injury includes a display screen that displays an image of a dynamic target for a subject to track using a sensing component and an image of a tracker representing the subject's tracking of the dynamic target and a data acquisition unit that receives, from the sensing component, tracking data representing the subject's tracking of the dynamic target. The system also includes a parameter generating unit that determines, based on target data and the tracking data, a model value indicative of the subject's corrective actions in response to deviations between the tracker and the dynamic target over a period of time, a memory that contains multi-subject model values, and a comparison unit that compares the model value to the multi-subject model values to determine a likelihood that the subject has a brain injury.

In some embodiments, a system for screening of a brain injury includes a sensing component configured to detect and transmit tracking data representing a subject's tracking of a dynamic target on a display. The system also includes an electronic device in communication with the sensing component, the electronic device including a display, a memory, and a programmable controller to carry out the steps of displaying on the display an image of a dynamic target for a subject to track using the sensing component, receiving, from the sensing component, tracking data representing the subject's tracking of the dynamic target, displaying on the display, in real time, an image of a tracker on the display representing the subject's tracking of the dynamic target, determining a model value derived from the tracking data and indicative of the subject's corrective actions in response to deviations between the tracker and the dynamic target over a period of time, comparing the model value to multi-subject model values, and outputting a screening indicator representing the likelihood that the subject has a brain injury based on the compared model values.

BRIEF DESCRIPTION OF THE DRAWINGS

FIG. 4 illustrates one or more screening systems communicating via wireless communication with a centralized online server in accordance with some embodiments.

FIG. 5 illustrates one or more screening systems communicating via wireless communication with one or more dispersed online servers in accordance with some embodiments.

FIG. 12 is a table comparing classification results from a feedback response model that captures subjects' response to error to conventional evaluation methods using the same test participants in accordance with some embodiments.

DETAILED DESCRIPTION OF THE INVENTION

Figure 1:
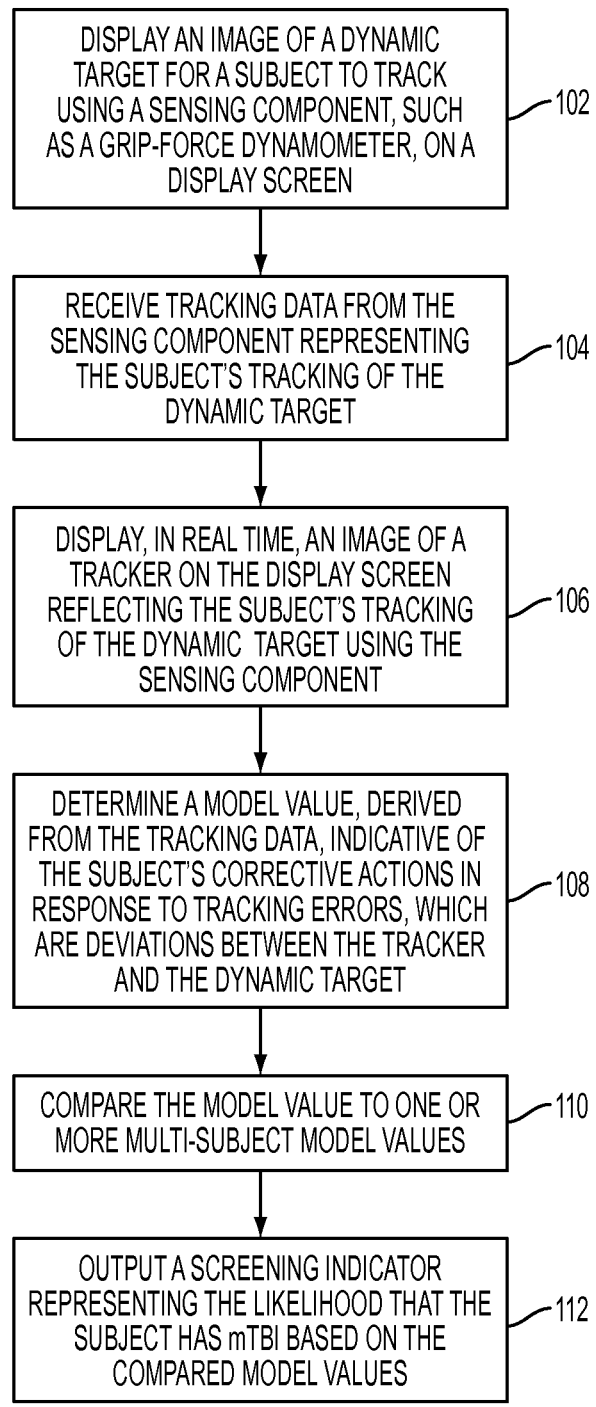
FIG. 1 is a flow diagram illustrating a process for rapid screening of a brain injury by using a dynamic motor tracking task in accordance with some embodiments.

In the following description of the disclosure and embodiments, reference is made to the accompanying drawings in which it is shown by way of illustration specific embodiments that can be practiced. It is to be understood that other embodiments and examples can be practiced and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units, but do not preclude the presence or addition of one or more other features, integers, steps, operations, elements, components, units, and/or groups thereof.

There is a need to make easy, reliable, and rapid screening for mTBI due to the nature and symptoms of the injury. For example, if a serviceman in the battlefield suffers a blow to the head but does not exhibit immediate signs of injury, the serviceman may remain untested and untreated for a significant period of time following the traumatic exposure. During this time, the injury may manifest to hinder his/her performance and put him/her at risk of further, more severe, brain damage from a second accident. Therefore, an ability to easily, reliably, and rapidly detect for mTBI is of great need to entities such as the military. Such techniques can be administered by any level of caregiver in any environment within a matter of minutes to provide a rapid and reliable diagnosis, thereby enhancing the likelihood of a full and speedy recovery down the road. Further, such techniques can be used to easily monitor an individual's recovery progress over time by a comparison between a present screening result and one or more previous screening results.

Embodiments of a screening system, processing and sensing components for such a system, and associated processes for using such a system are described. The screening system may perform a variety of applications, such as one or more of the following: screening for a brain injury, monitoring recovery progress from a brain injury, screening for drug and/or alcohol intoxication, and gathering individual baseline motor response data. Further, the screening system may perform a variety of applications, such as one or more of the above listed applications, without any or with only minimal modifications made to its processing and sensing components and its associated processes.

In some embodiments, the screening system is used to screen for a brain injury, in particular mild traumatic brain injury (mTBI), by utilizing a simple motor tracking task. For example, because an onset of mTBI is generally accompanied by a sudden decline in motor skills such as reflexes, coordination, and balance, a mTBI-positive individual may be expected to commit more "errors" during a motor tracking task than a non-mTBI counterpart. Further, the variability in motor tracking ability may be more prominent when the intended tracking target is an unpredictably or randomly moving dynamic target. Therefore, the screening system utilizes a simple dynamic tracking task, preferably using an unpredictable or random target, to measure the deviations—i.e., the tracking errors—between, for example, a subject's actual input force and the intended target force. These deviations, or tracking errors, may comprise, for example, delays in response time, overly strong input force, overly weak input force, overly fast change in input force, and/or overly slow change in input force.

After gathering a subject's tracking error measurements, the screening system may generate one or more representative numerical values summarizing the subject's performance. The representative value—i.e, a model value—may in turn be compared to representative values of pre-existing measurements from individuals of known diagnoses. If the pre-existing measurements comprise measurements from both mTBI-positive and mTBI-negative individuals, measurements from each group may be expected to cluster together amongst its respective group, thereby forming two largely distinct measurement clusters. The subject's performance may then be compared to the pre-existing representative values and sorted into the more similar group. If the subject's representative value falls clearly within the cluster of non-mTBI individuals, the screening system may output an mTBI-negative diagnosis for the subject. If the subject's representative value falls clearly within the cluster of mTBI-positive individuals, the screening system may output an mTBI-positive diagnosis for the subject. Otherwise, the screening system may output a diagnosis with a low confidence value, prompt the subject for a re-screen, and/or request the subject to seek clinical testing. The entire screening process may be administered in a matter of minutes in almost any environment.

While the present disclosure focuses on the use of the disclosed screening system to screen for mTBI, it should be understood that the screening system may also be used to test for other types of physical and/or mental disability or impairment. For example, the screening system may be used for rapid screening of drug and/or alcohol use. Drug and/or alcohol intoxication, even in a small degree, may hinder or interference with a person's regular motor tracking ability. Therefore, the screening system may be used to perform a screening process, without any modifications, to easily, reliably, and rapidly screen drug and/or alcohol intoxication. The screening system may also be used to screen for mild cognitive impairments, motor disorders such as early Alzheimer's, Parkinson's, and Huntington's diseases, post-traumatic stress disorder, and sleep deprivation.

Figure 2:
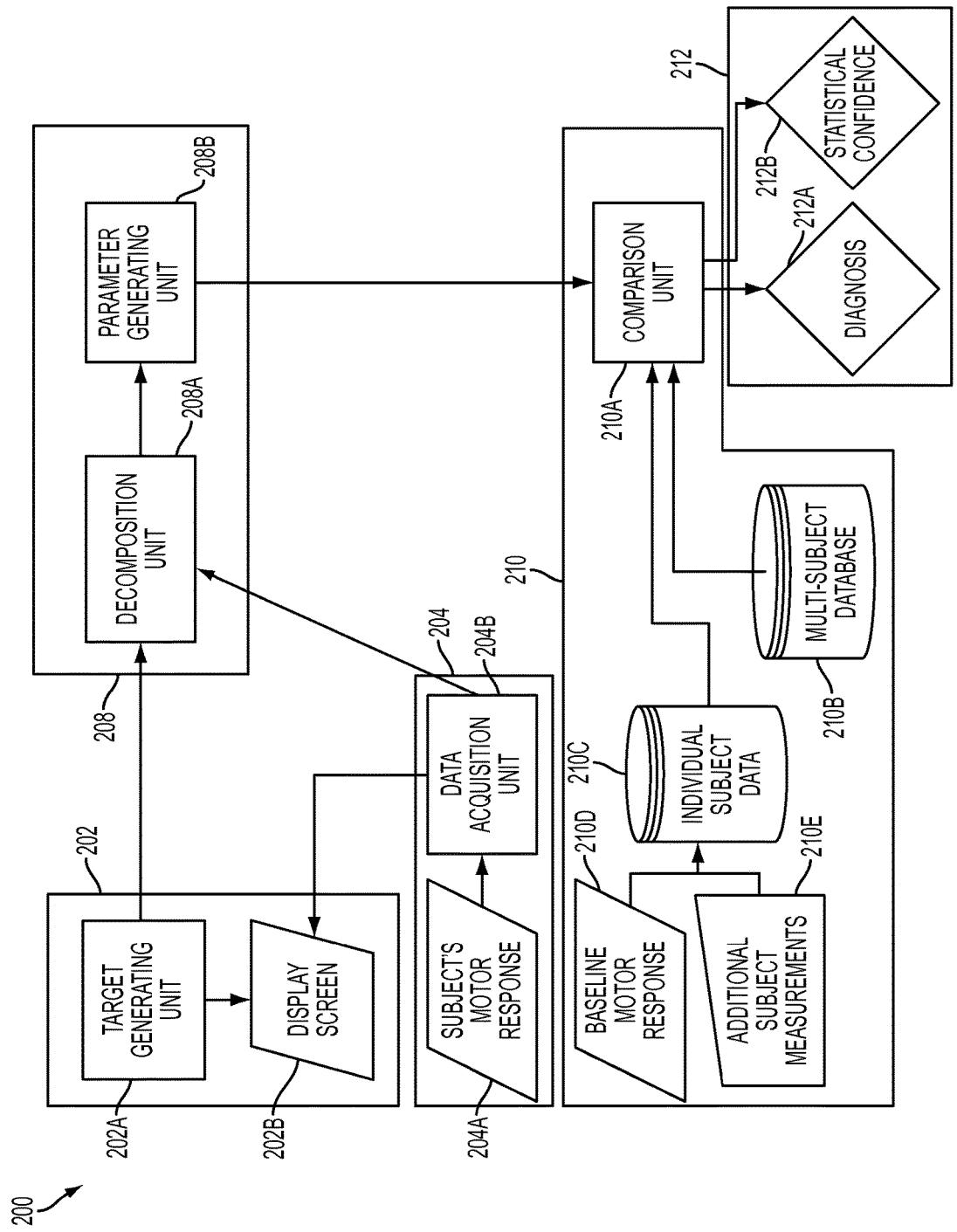
FIG. 2 is a block diagram illustrating multiple components of a process for rapid screening of a brain injury by using a dynamic motor tracking task in accordance with some embodiments.

FIGS. 1 and 2 are, respectively, a flow diagram and a block diagram illustrating a screening process in accordance with some embodiments. The screening process may be performed by a screening system implementing a dynamic motor tracking task for rapid screening of a brain injury, in particular mild traumatic brain injury (mTBI). The screening system comprises a processing component connected to a sensing component. In some embodiments, the processing component and the sensing component may be part of the same device. The processing component may in turn comprise a display screen and a computing device. In some embodiments, the display screen and the computing device may be part of the same device. In some embodiments, the display screen and the computing device may be part of separate devices.

The processing component may be a desktop computer, laptop computer, tablet computer, smartphone, smartwatch, and/or any other electronic device or a combination thereof capable of performing data collection, data processing, and data analysis. The processing component may include a target generating unit 202A, a data acquisition unit 204B, a decomposition unit 208A, a parameter generating unit 208B, a comparison unit 210A, and a memory. Each "unit" may include computer software, hardware, combinations thereof, or a component of a computer program capable of performing a particular function that may be stored on one or more non-transitory computer readable mediums. Thus, while several different "units" are mentioned for the sake of clarity, it is to be understood that the functions of any combinations of the various units, which may include a target generating unit 202A, a data acquisition unit 204B, a decomposition unit 208A, a parameter generating unit 208B, and a comparison unit 210A, may be performed by a single hardware component, for example a microprocessor.

The processing component communicates with a memory that has stored therein one or more software program, which command one or more microprocessors within the processing component to execute the required steps of the disclosed screening process via various functional "units," described in more detail below. The software programs for executing the disclosed screening process may be available for download from an online application store, for example APP STORE for APPLE iOS and GOOGLE PLAY STORE for ANDROID. In some embodiments, the software program for executing the disclosed screening process may be available for installation via an optical data storage disc, such as a compact disc (CD), or other portable storage devices such as a Universal Serial Bus (USB) flash drive. In some embodiments, the software program for executing the disclosed screening process may be pre-installed in one or more electronic devices manufactured to function solely as the disclosed processing component.

The sensing component may be any input device or component, including a force-detecting dynamometer or other force sensor, a push-or-pull sensitive device, including a video-game controller or touch screen, an eye-tracking device, a body movement measurement device, and/or any other device capable of detecting user-applied force, power, and/or torque and changes in user-applied force, power, and/or torque, or any device capable of detecting movements, gestures, and/or signals made by the user.

In some embodiments, the sensing component may be a grip-force dynamometer. The grip-force dynamometer detects force applied and changes in force applied by the grip of a user and transmits this information as tracking data to the processing component. For example, the grip-force dynamometer may be a JAMAR dynamometer or a similar device. In some embodiments, the sensing component may be a push-sensitive device. The push-sensitive device detects force applied and changes in force applied by a push, using the hand, arm, and/or foot, of a user and transmits this information as tracking data to the processing component. For example, the push-sensitive device may be a button that a user can push using the hand, arm, and/or foot. In some embodiments, the sensing component may be an eye-tracking device. The eye-tracking device detects the position and changes in position of one or both eyes of a user. For example, the eye-tracking device may be a wearable glass with one or more sensors tracking the movements of one or both eyes. In some embodiments, the sensing component may be a body motion measurement device. The body motion measurement device may track and/or measure bodily movements, gestures, signs and/or signals made by a user. For example, the body motion measurement device may be an accelerometer-based device capable of measuring bodily activity ranging from subtle vibrations to large gestures and movements.

In some embodiments, the screening system may comprise a processing component and a sensing component that are part of a single electronic device. Further, the single electronic device may be a portable device. For example, the disclosed screening process may be performed by a smartphone with a gesture or eye-tracking input capability. The smartphone is a computing device that may function as the processing component, and the gesture or eye-tracking sensor of the smartphone may function as the sensing component.

At step 102 of FIG. 1 and corresponding components 202 of FIG. 2, the screening system is carrying out a dynamic motor tracking task. During the motor tracking session, the processing component displays on a display screen 202B a graphical image of a dynamic target. A subject, positioned at close proximity to the display screen 202B such that the dynamic target is clearly visible, tracks the dynamic target via a sensing component. The movement pattern of the dynamic target on the display screen 202B may be controlled by instructions transmitted from a target generating unit 202A within the processing component in the form of target data. The target data transmitted from the target generating unit 202A to generate a particular movement pattern for a dynamic target—i.e., a particular target mode—may be based on computer software pre-programmed into the target generating unit 202A.

Further, the target generating unit 202A may be programmed with a plurality of different target modes, each target mode transmitting its own unique target data corresponding to a unique target movement pattern. For example, each target mode or a particular target mode may be programmed to maximize the accuracy of the final diagnosis of the screening system for individuals of a certain pre-defined group. In some embodiments, each target mode or a particular target mode may be tailored to a particular population, community, group, or organization. Differentiating among persons of different groups or organizations, for example, may compensate for the fact that a professional athlete generally possesses superior motor skills to a typical non-athlete. Comparing the motor response of a professional athlete to that of a typical non-athlete may not be appropriate because of inherent differences in the level of motor skill. Therefore, a screening system used by the military, for example, may contain a processing component programmed with one or more target modes tailored specifically for military personnel. Similarly, a screening system used by a sporting league or institution, such as the National Football League (NFL) or the National Collegiate Athletic Association (NCAA)'s football program, may be programmed with one or more target modes tailored specifically for football players.

In some embodiments, each target mode or a particular target mode may be tailored to a particular characteristic of a group. A characteristic may include, but is not limited to, gender, age, height, weight, and/or ethnicity. Differentiating among persons of different age groups, for example, may compensate for the fact that a person's motor skills naturally decline with age. For instance, there may be separate target modes tailored specifically for persons of different age groups, such as ages 10-14, ages 15-19, ages 20-39, ages 40-59, and ages 60 and above. Similarly, there may be separate target modes tailored specifically for persons within a specified height range and/or within a specified weight range. In some embodiments, each target mode or a particular target mode may be tailored to enhance the level of fun and/or challenge of the motor tracking task. For example, it may be easier to gather tracking data from children when they are more engaged in successfully completing the motor tracking task.

In some embodiments, the target data transmitted from the target generating unit 202A may be a sequence of random numbers generated by software code designed to generate a sequence of numbers that lack any pattern. For example, the target generating unit may be programmed with a random number generator having one or more different computational methods for generating random data. A particular computational method for generating random data may be based on, for instance, a pseudorandom number generator (PRNG), a deterministic random bit generator (DRBG), or the like.

In some embodiments, the computer software for a particular target mode may be representative of an algorithm. The algorithm may generate an output, for example a target force, as a function of time. In some embodiments, an algorithm may generate an output, as a function of time, which causes the dynamic target to move in an unpredictable pattern. An unpredictable pattern represents an irregular, non-periodic, and non-repetitive movement such that the subject cannot predict in advance the target's future path. Thus, an unpredictable pattern tests a subject's feedback response; that is, how they respond to, and correct for, errors when performing the task. In some embodiments, an algorithm may generate an output, as a function of time, which causes the dynamic target to move in a predictable pattern. A predictable pattern represents a regular, periodic, and repetitive movement such that the subject can predict in advance the target's future path. Thus, a predictable pattern tests a subject's feedforward, or predictive, response; that is, how well a subject can predict where the target will be at some time in the future.

Figure 3A:
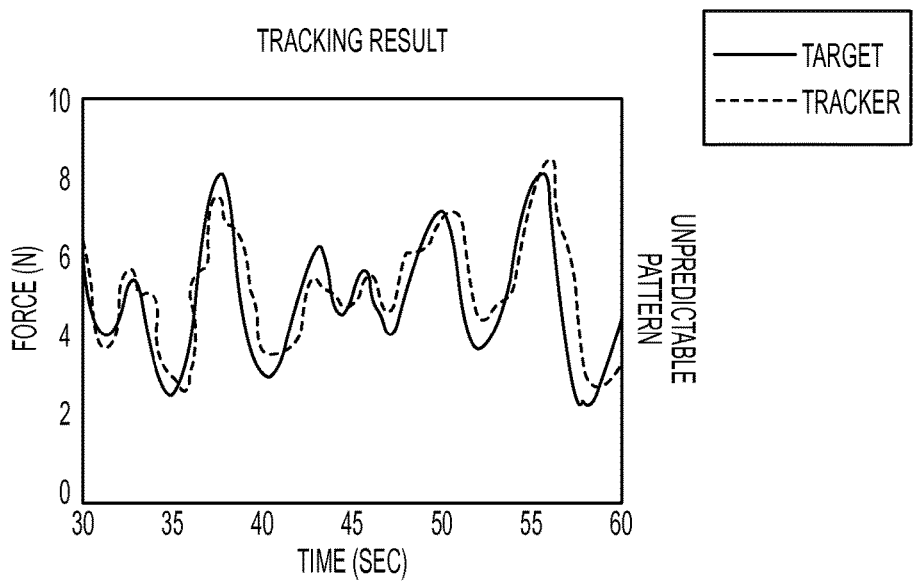
FIGS. 3A and 3B are graphical depictions of the relative difference in force between a subject's input force and the intended target force in accordance with some embodiments.
Figure 3B:
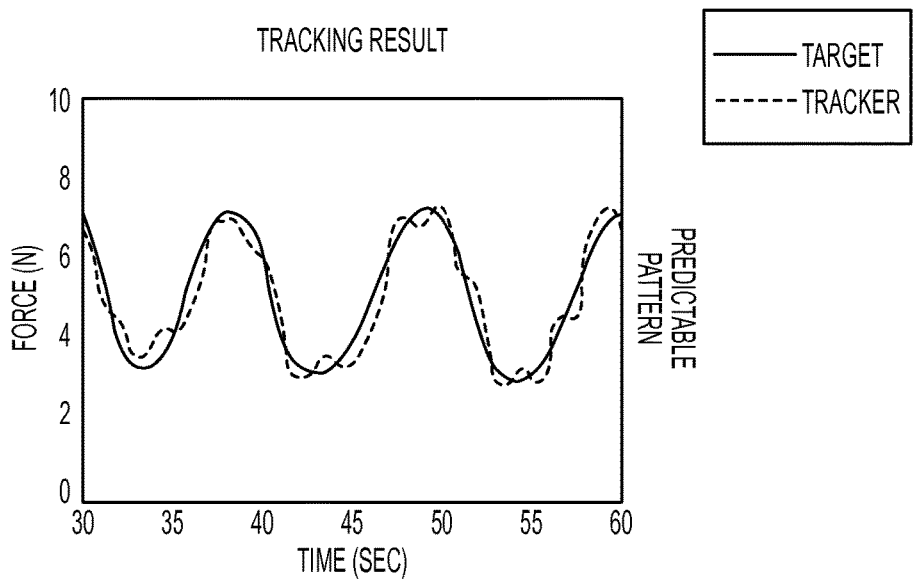

In some embodiments, an algorithm may use a combination of one or more continuous wave functions, including sine waves, square waves, triangle waves, and/or constants that produce an unpredictable movement pattern. It may also include step functions, wavelets, or other perturbations. For instance, the unpredictable algorithm may be similar in form to the following mathematical equation measuring force: $F(t)=\sin(2\pi f_1 t)+\sin(2\pi f_2 t)+\sin(2\pi f_3 t)+C$, where $f_1=0.2335$ Hz, $f_2=0.37$ Hz, $f_3=0.45$ Hz, and C is a constant that equals 5% of a subject's maximum grip-force, measured in Newtons, determined at the beginning of the motor tracking task. The frequencies $f_1$, $f_2$, and $f_3$ should be visually detectable by participants, and within a range that they can feasibly respond to (e.g., 0.1-10 Hz). A target mode based on this exemplary algorithm may generate an unpredictable movement pattern as represented graphically in FIG. 3A, which relates user-applied force to time. In some embodiments, the algorithm may represent a single periodic sine and/or cosine wave, or a combination of one or more continuous wave functions, including sine waves, square waves, triangle waves, and/or constants that produce a predictable movement pattern. For example, the algorithm may be one similar in form to the following mathematical equation: $F(t)=2\sin(2\pi ft)+C$, where $f=0.30$. The frequency f should be visually detectable by participants, and within a range that they can feasibly respond to (e.g., 0.1-10 Hz). A target mode based on this exemplary algorithm may generate a repetitive movement pattern as represented graphically in FIG. 3B, which relates user-applied force to time.

A motor tracking task based on a particular target mode may be programmed to run for a particular period of time. In some embodiments, a target mode may be programmed to generate target data for a time period measured in minutes, for example less than 10 minutes, less than 5 minutes, and/or less than 2 minutes. In some embodiments, a target mode may be programmed to generate target data for a time period measured in seconds, for example less than 45 seconds, less than 30 seconds, and/or less than 15 seconds. In some embodiments, an operator or user of the screening system may be given an option to select a particular time period from a plurality of choices to accommodate for differing environments and circumstances. In some embodiments, an operator or user of the screening system may be able to enter any customized time period before the beginning of the tracking session via a keyboard input, mouse input, touchscreen input, voice command, or the like. In some embodiments, the examination time period may be easily adjustable by the operator before and/or during the tracking session in order to accommodate for differences in condition among tracking sessions. In some embodiments, some or all available target modes may include an additional "practice phase" period, which may be less than a minute, at the beginning of the tracking session to allow the subject to develop familiarity with using the sensing component to track the displayed dynamic target.

At step 104 of FIG. 1 and corresponding components 204 of FIG. 2, a data acquisition unit 204B of the processing component may receive from the sensing component, in the form of tracking data, information representing a subject's motor tracking of a dynamic target 204A during a motor tracking task. The transmission of the tracking data from the sensing component to the data acquisition unit 204B may occur in real time. In some embodiments, the tracking data may be transmitted from the sensing component to the data acquisition unit 204B via a cable connecting the sensing component to the processing component, including but not limited to a Universal Serial Bus (USB) connection. In some embodiments, the tracking data may be transmitted from the sensing component to the data acquisition unit 204B via wired internet, for example a wired local area network (LAN), and/or wireless communication, for example Global System for Mobile Communications (GSM), Enhanced Data GSM Environment (EDGE), Bluetooth, and Wireless Fidelity (Wi-Fi).

The processing component may store the tracking data, retrieved from the data acquisition unit 204B, and the corresponding target data, retrieved from the target generating unit 202A, in a database 210B. For example, the processing component may store the tracking data and the corresponding target data in a database 210B for future use. The screening system may rely on comparing a subject's modeled motor tracking result to a plurality of known measurements in making a diagnosis. Therefore, it may be important for the screening system to have access to an abundance of measured tracking data of a plurality of individuals. Accordingly, in some embodiments, the screening system may automatically store the subject's measured tracking data, together with its corresponding target data, in a database 210B. In some embodiments, the screening system may ask the operator or subject, via a visual or audio message, whether it should or should not store the subject's measured tracking data and corresponding target data in a database 210B.

Given the importance of gathering and storing an abundance of measured tracking data from a plurality of individuals, including both mTBI-positive and mTBI-negative individuals, the screening system may be used simply to collect data. Therefore, in some embodiments, the screening system may present the operator or subject, via a visual or audio message, with an option to stop the screening process upon completion of the motor tracking task. Further, in some embodiments, the screening system may be used, without modification, to gather individual baseline motor response data 210D, which may be incorporated by the comparison unit 210A at a later step in the screening process.

The database 210B may be stored in one or more memories. For example, the database 210B may be stored in one or more non-volatile memories contained within or connected to the processing component of the screening system. The memory may include but is not limited to a hard disk drive (HDD), a solid-state drive (SSD), a Universal Serial Bus (USB) flash drive, and/or a Secure Digital (SD) memory card.

As illustrated in FIGS. 4 and 5, the database 210B may additionally and/or alternatively be stored in one or more online servers 420, 520, 522 and/or 524. Because the screening system may rely on comparing a subject's modeled motor tracking result to a plurality of known measurements in making a diagnosis, the system may require constant updates in order to incorporate newly-gathered measurements. As the amount of measured data increases, it may be impractical to constantly update the system with the new data or store the increasing amount of data within the processing component itself. If all or a majority of the measurements were stored and accessible online, however, all screening systems connected to the online servers may easily have access to the most up-to-date information and may retrieve them accordingly.

As illustrated in FIG. 4, in some embodiments, system 400 includes one or more online servers that may be hosted at a centralized location 420 and accessible by screening systems 402, 404 and 406 over network 410, such as the internet. For example, online servers may be hosted by a single institution that gathers and stores tracking data generated specifically from the disclosed screening system. As illustrated in FIG. 5, in some embodiments, system 500 includes one or more online servers may be dispersed throughout a plurality of host locations 520, 522 and/or 524 and accessible by screening systems 502 over network 510. For example, data regarding some users may be stored by a healthcare provider, data regarding some users may be stored by an institution, organization, or company, and data regarding some users may be stored by a cloud storage service provider.

The processing component may transmit the tracking data and the corresponding target data to an online server via wired internet, for example a wired local area network (LAN), and/or wireless communication, for example Wireless Fidelity (WiFi) and mobile telecommunications technology such as Long-Term Evolution (LTE). The transmitted tracking data and corresponding target data may simply be stored in a user-profile database 210B contained in an online server for potential future use. Additionally, the transmitted tracking data and corresponding target data may be accessed by a processing component located at a remote location to perform a remote diagnosis.

Figure 9:
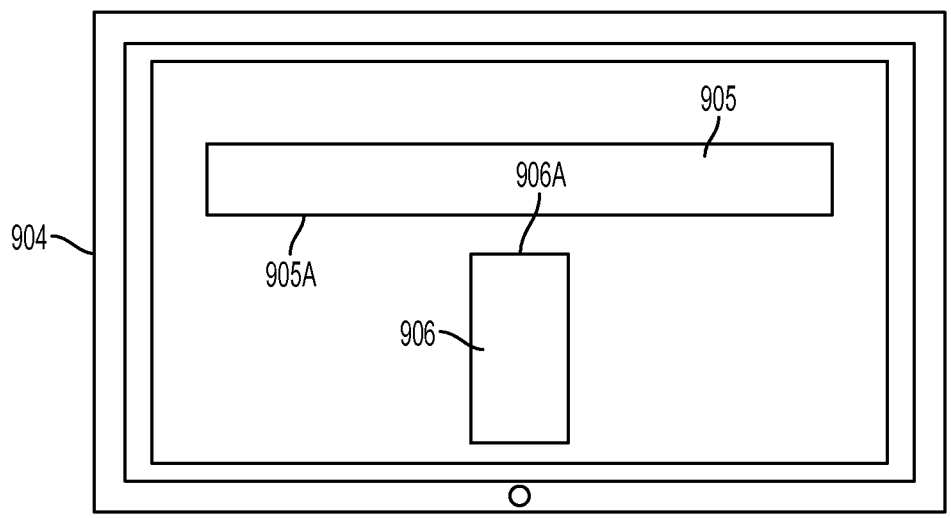
FIG. 9 is an exemplary display screen showing a graphical image of a dynamic target and a graphical image of a subject-controlled tracker in accordance with some embodiments.

At step 106 of FIG. 1, the processing component displays at display screen 202B of FIG. 2, in real time, a graphical image of a tracker as the subject performs a motor tracking task. The tracker may be a visual representation of the subject's tracking of the dynamic target via the sensing component. Visually displaying the subject's tracking of the dynamic target in real time enables the subject to continuously observe his/her response to the movement patterns of the dynamic target and react to his/her errors in tracking the dynamic target. An exemplary embodiment of a tracker and a dynamic target displayed and interacting on a display screen 202B of the processing component is illustrated in FIG. 9 and further described below. In some embodiments, the graphical images of the tracker and dynamic target may be rendered on the same display screen. In some embodiments, the graphical images of the tracker and the dynamic target may be rendered on different sections of the same display screen. In some embodiments, the graphical images of the tracker and the dynamic target may be rendered on different display screens.

At step 108 of FIG. 1 and corresponding components 208 of FIG. 2, the motor tracking task is complete. The gathered tracking data and the corresponding target data are both transmitted to a parameter generating unit 208B from the data acquisition unit 204B and from the target generating unit 202A, respectively. In some embodiments, the tracking data may be transmitted directly from the data acquisition unit 204B to the parameter generating unit 208B and the corresponding target data may be transmitted directly from the target generating unit 202A to the parameter generating unit 208B.

In some embodiments, the data acquisition unit 204B may first transmit the tracking data, and the target generating unit 202A the corresponding target data, to a decomposition unit 208A. The decomposition unit 208A may be, for example, a filtering and decomposition component within the processing component that receives signal data and converts the signal data into a plurality of meaningful data components. The filtering and decomposition component may receive the tracking data and the target data and filter and decompose both data into a plurality of tracking data components and a plurality of target data components, respectively. For example, the tracking and target data may each be filtered and decomposed by the decomposition unit 208A into position, velocity, and acceleration, errors in position, velocity, and acceleration (differences from the target), and lag. The various tracking data components and the various target data components may then be transmitted to the parameter generating unit 208B.

Once the tracking data and the corresponding target data, or the tracking data components and the corresponding target data components, have been received, the parameter generating unit 208B parameterizes the subject's response to errors via a feedback response model on the received data or data components to quantify a value for each model parameter. The model value may consist of a single or multiple numerical values representing a single or multiple model parameters. For example, a model value may be a fitted model parameter that optimizes the fit of the feedback response model to the subject's tracking data and the target data, or to the subject's tracking data components and corresponding target data components.

In some embodiments, the feedback response model may correlate the subject's responses to committed tracking error, wherein tracking error represents differences between the tracking data and the target data, or differences between the tracking data components and the corresponding target data components. For example, if the sensing component is a force-detection device such as a grip-force dynamometer, the tracking error may be the difference between the intended target force and the actual subject-applied force. More specifically, the feedback response model may represent a feedback error learning technique that models a subject's feedback response, as opposed to a feedforward response, through a linear parameterization that maps errors in position and errors in velocity into corrective accelerations.

In some embodiments, the tracking data and the target data may first be filtered or decomposed into a plurality of data components before reaching the parameter generating unit 208B. For example, a zero-phase digital filtering using a second-order Butterworth filter with a 2 Hz cutoff frequency may be performed on the data. Following a filtering or decomposition of the data, the parameter generating unit 208B implements a feedback response model using the received tracking data components and target data components to quantify a plurality of model values. The plurality of model values may be fitted model parameters that optimize the fit of the feedback response model to the subject's tracking data components and the target data components.

The feedback response model may correlate the subject's responsive actions to correct deviations, i.e., the tracking error, between the subject's actual input, represented by the tracking data and rendered graphically on a display screen as the tracker, and the subject's intended target input, represented by the target data and rendered graphically on a display screen as the dynamic target. In some embodiments, the feedback response model may correlate the subject's responsive actions to correct deviations between the actual input position and the intended positional target. In some embodiments, the feedback response model may correlate the subject's responsive actions to correct deviations between the actual input velocity and the intended velocity target. In some embodiments, the feedback response model may correlate the subject's responsive actions to correct deviations between the actual input acceleration and the intended acceleration target. In some embodiments, the feedback response model may correlate the subject's responsive actions to correct deviations between the actual input force and the intended force target. In some embodiments, the feedback response model may correlate the subject's responsive actions to correct deviations between the actual input pressure and the intended pressure target. In some embodiments, the feedback response model may correlate the subject's responsive actions to correct deviations between the actual input gesture and the intended gesture target. In some embodiments, the feedback response model may correlate the subject's responsive actions to correct deviations between the actual input eye movement and the intended eye movement target. In some embodiments, the feedback response model may correlate the subject's responsive actions to correct deviations between the actual input arm movement and the intended arm movement target.

In some embodiments, the feedback response model may transform errors in position into corrective changes in velocity which reduce the overall tracking error. In some embodiments, the feedback response model may transform errors in position and/or errors in velocity into corrective accelerations which reduce the overall tracking error. Here, position refers to any deviation from the target; velocity refers to the derivative of that deviation; acceleration refers to the second derivative of that deviation. In some embodiments, the feedback response model may further incorporate lag, representing the time difference that minimizes the subject's actual tracking input and the intended target.

A generated model value may be a numerical value representative of the subject's performance during the motor tracking task. In other words, a subject's performance may be summarized by one or more numerical values—i.e., one or more model values—in order to compare the subject's motor tracking performance with that of tested subjects. For example, a non-mTBI individual's motor tracking performance may result in a relatively low model value. On the other hand, an mTBI-positive individual's motor tracking performance may result in a relatively high model value. In some embodiments, a subject's motor tracking performance may be represented by a plurality of model values, each model value representative of a particular aspect of the subject's motor tracking performance. For example, a positional error model value may be indicative of the subject's performance with respect to his/her accuracy regarding the degree of actual applied force in relation to a displayed target force. A velocity error model value may be indicative of the subject's performance with respect to his/her accuracy regarding the degree of change in actual applied force in relation to a displayed change in target force.

An exemplary feedback response model, in mathematical form, may be represented by an algorithm equivalent to or similar to the following exemplary mathematical equation: $\ddot{x}_{(t)} = -K_p(x_{(t-\tau)} - x_{d(t-\tau)}) - K_d(\dot{x}_{(t-\tau)} - \dot{x}_{d(t-\tau)})$. This exemplary feedback response model transforms errors in position, $x_{(t-\tau)} - x_{d(t-\tau)}$, and errors in velocity, $\dot{x}_{(t-\tau)} - \dot{x}_{d(t-\tau)}$, into corrective accelerations, $\ddot{x}_{(t-\tau)}$, which reduce the subject's overall tracking error. x and $\dot{x}$ represent the position and velocity, respectively, of the subject's input via the sensing component. $x_d$ and $\dot{x}_d$ represent the position and velocity, respectively, of the target. This exemplary feedback response model further accounts for lag, $\tau$, which is quantified as the time shift that minimizes the root-mean-square error between the subject's input and the target. The errors in position, $x_{(t-\tau)} - x_{d(t-\tau)}$, and velocity, $\dot{x}_{(t-\tau)} - \dot{x}_{d(t-\tau)}$, are correlated to the corrective accelerations, $\ddot{x}_{(t)}$, by two fitted model parameters, $K_p$ and $K_d$, which, when quantified, are the model values. A zero-phase digital filtering, using for example a second-order Butterworth filter with a 2 Hz cutoff frequency, may be performed on the raw position before differentiating.

In some embodiments, the feedback response model may use a Gauss-Jordan method to optimize for a model value that minimizes the mean-squared difference between the predicted corrective responses and actual corrective responses of the subject. Prediction accuracies may then be quantified using the correlation between the predicted and actual corrective responses. For example, the exemplary feedback response model may use a Gauss-Jordan method to optimize for values of $K_p$ and $K_d$ that minimize the mean-squared difference between the predicted corrective accelerations and actual corrective accelerations of the subject. Prediction accuracies may then be quantified using the correlation between the predicted and actual corrective accelerations.

At step 110 of FIG. 1 and corresponding components 210 of FIG. 2, the model value or the plurality of model values generated by the parameter generating unit 208B are transmitted to a comparison unit 210A, which compares the model value to one or more corresponding multi-subject model values in order to determine the subject's diagnosis.

As described previously, a model value represents a representative numerical value summarizing the subject's performance from the motor tracking task. A subject's generated model value may in turn be compared to model values from pre-existing measurements of known individuals. If the pre-existing measurements comprise measurements from both mTBI-positive and mTBI-negative individuals, measurements from each group may be expected to cluster together amongst its respective group, thereby forming two largely distinct measurement clusters. The subject's performance may then be compared to the pre-measured performances and sorted into the more similar group. If the subject's model value falls clearly within the cluster of mTBI-negative individuals, the screening system may output an mTBI-negative diagnosis for the subject. If the subject's representative value falls clearly within the cluster of mTBI-positive individuals, the screening system may output an mTBI-positive diagnosis for the subject. Otherwise, the screening system may output a diagnosis with a low confidence value, prompt the subject for a re-screen, and/or request the subject to seek clinical testing.

In some embodiments, the comparison unit 210A may implement a machine learning predictor, which may be trained on previously standardized multi-subject model values, on the subject's model value and the corresponding multi-subject model values to determine a diagnosis for the subject. In some embodiments, the machine learning predictor may be a statistical classifier, for example a Gaussian Process classifier, which is trained on previously standardized model values. The statistical classifier may use a constant mean function and a squared exponential covariance function with an Automatic Relevance Determination (ARD) distance measure. The statistical classifier may be adapted for binary classification with a cumulative Gaussian likelihood function and inference by Expectation Propagation. The classification analysis may be performed by selecting the most likely class among mTBI and non-mTBI control groups. Further, the classification analysis may be performed by using the Gaussian Processes for Machine Learning (GPML) library for MATLAB.

For example, a parameter generating unit 208B implementing the exemplary feedback response model may generate and transmit model values $K_p$ and $K_d$ to the comparison unit 210A. After obtaining the model values $K_p$ and $K_d$, the comparison unit 210A, which may be a machine learning predictor, may implement a Gaussian Process classifier that is trained on previously standardized multi-subject model values for $K_p$, $K_d$, and $\tau$. The classifier may use a constant mean function, and a square exponential covariance function with an Automated Relevance Determination (ARD) distance measure. The length scales for $K_p$ and $\tau$ may initially be set to 1, and the length scale for $K_d$ may be set to 5. $K_p$ and $K_d$ may range from 0.1 to 100. The Gaussian Process classifier may be adapted for binary classification with a cumulative Gaussian likelihood function and inference by Expectation Propagation. The classification analysis may be performed by selecting the most likely class among mTBI and mTBI-negative control groups. Further, the classification analysis may be performed by using the Gaussian Processes for Machine Learning (GPML) library for MATLAB.

Multi-subject model values may be model values of prior screening subjects, which may or may not include the current subject, stored in a database 210B. The prior screening subjects may comprise both non-mTBI controls and mTBI patients. In some embodiments, the database 210B may be stored in a non-volatile memory contained within or connected to the processing component. The memory may include but is not limited to a hard disk drive (HDD), a solid-state drive (SSD), a Universal Serial Bus (USB) flash drive, and/or a Secure Digital (SD) memory card. In some embodiments, database 210B may be stored in one or more online servers hosted at a centralized location. The processing component may retrieve the multi-subject model values when needed from the online server via wired internet, for example a wired local area network (LAN), and/or wireless communication, for example Wireless Fidelity (WiFi) and mobile telecommunications technology such as Long-Term Evolution (LTE).

At step 112 of FIG. 1 and corresponding components 212 of FIG. 2, the processing component may output a screening indicator 212A representative of the diagnosis made by the comparison unit 210A. In some embodiments, the screening indicator 212A may display the diagnosis on a display screen as YES or NO, POSITIVE or NEGATIVE, or the like. In some embodiments, the screening indicator 212A may be accompanied by a statistical confidence interval 212B, for example a likelihood that the diagnosis is correct or incorrect. In some embodiments, the screening indicator 212A may be a recovery indicator or may be accompanied by a recovery indicator, wherein the recovery indicator is indicative of the recovery progress of the subject.

Figure 6:
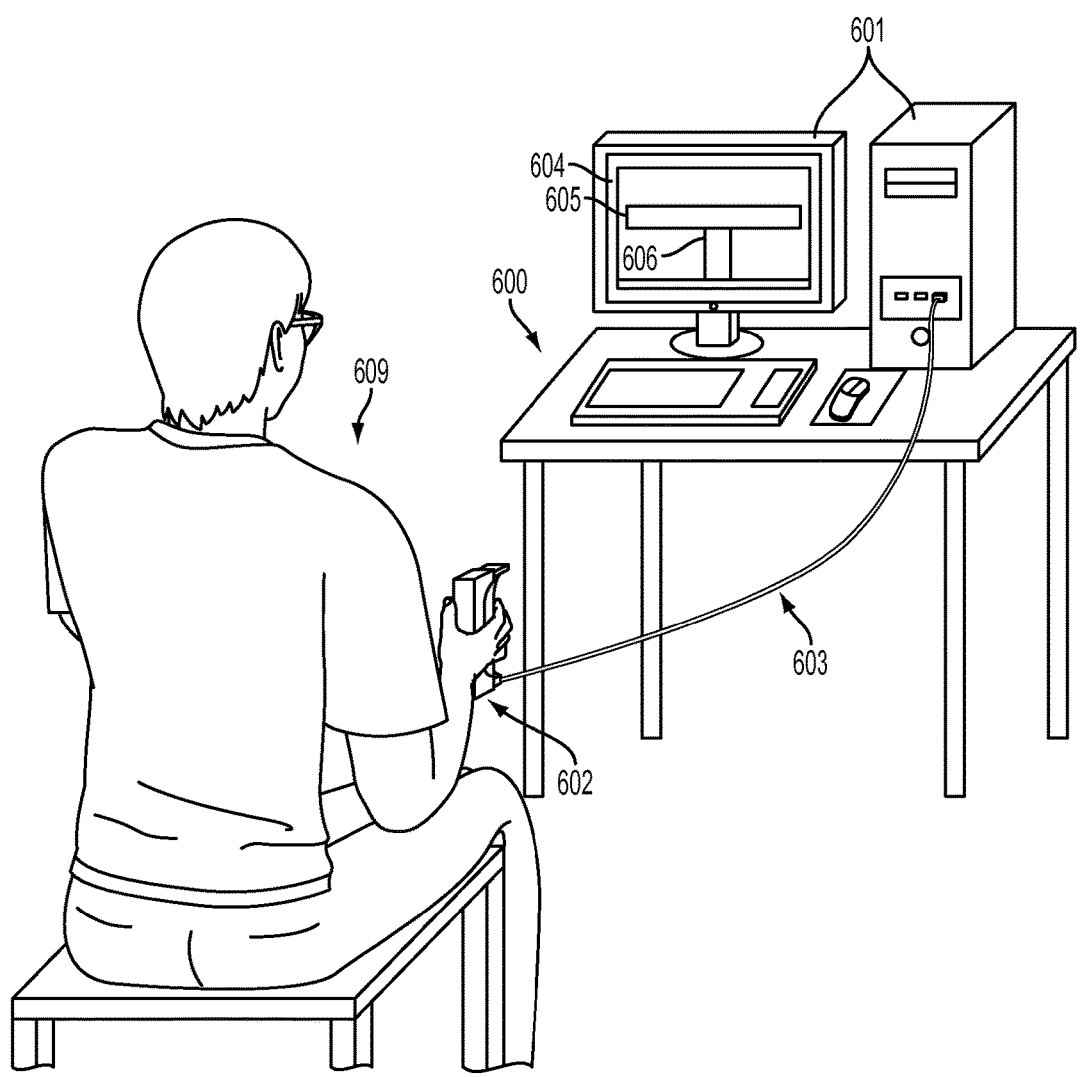
FIG. 6 illustrates an exemplary screening system for measuring and obtaining a subject's tracking data by using a handheld input device and a simple dynamic motor tracking task in accordance with some embodiments.

FIG. 6 is a perspective view illustrating a subject 609 performing a dynamic motor tracking task with a screening system 600, comprising a processing component 601 and a sensing component 602, in accordance with some embodiments. In some embodiments, the sensing component may be a grip-force dynamometer 602 as illustrated in FIG. 6. The grip-force dynamometer 602 detects changes in force applied by a hand grip of a subject and transmits this information, in real time, as tracking data to the data acquisition unit.

The subject 609, gripping the dynamometer 602 in one hand, watches a visual image of a dynamic target 605 moving in a pattern across a display screen 604 as instructed by the target generating unit (not shown). In some embodiments, the dynamometer 602 may transmit tracking data to the processing component 601 via a cable 603. In some embodiments, the dynamometer 602 may transmit tracking data to the processing component 601 via wired internet, for example a wired local area network (LAN), and/or wireless communication, for example Global System for Mobile Communications (GSM), Enhanced Data GSM Environment (EDGE), Bluetooth, and Wireless Fidelity (Wi-Fi).

The subject 609 adjusts his/her grip-force on the dynamometer 602 to track the image of the dynamic target 605 on the display screen 604. To accomplish this, the dynamometer 602 may contain a transducer that detects changes in the subject's grip-force and conveys this information, in real time, as tracking data to the data acquisition unit (not shown). The data acquisition unit then instructs the display screen 604 to display, in real time, an image of the subject-controlled tracker 606. In some embodiments, the tracker 606 may be a movable, changeable, or adjustable graphical image on the same display screen as the target 605. In some embodiments, the tracker 606 may be a movable, changeable, or adjustable graphical image on a different potion of the same display screen or on a different display screen from the target 605.

Figure 7:
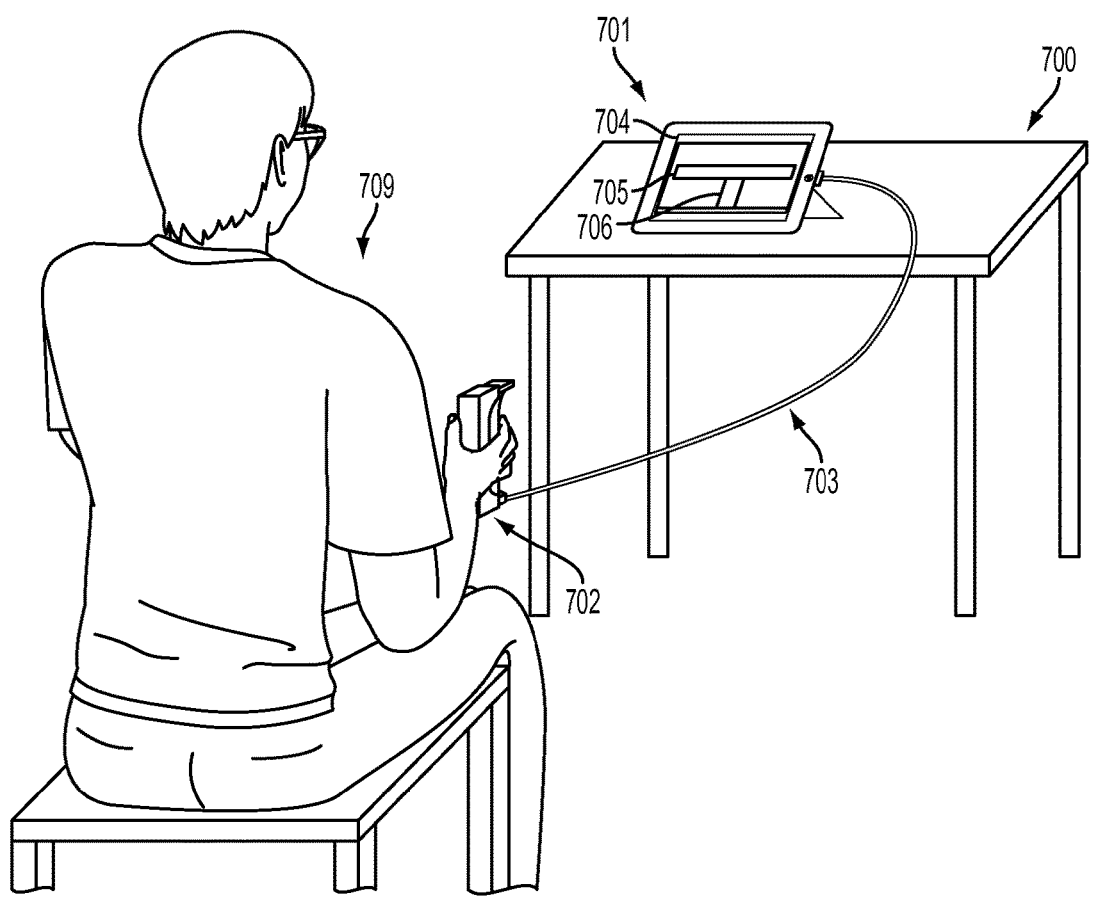
FIG. 7 illustrates a processing component that is a portable device being used to perform a screening process in accordance with some embodiments.

FIG. 7 is a perspective view illustrating a subject 709 performing a dynamic motor tracking task with a screening system 700, comprising a processing component 701 and a sensing component 702, wherein the processing component 701 is a portable device, in accordance with some embodiments. The processing component may consist of one or more portable electronic devices with a display screen. The portable electronic device may be a laptop computer, tablet computer, smartphone, and/or smartwatch that may include a target generating unit, a data acquisition unit, a decomposition unit, a parameter generating unit, a comparison unit, and a memory. While several different "units" are mentioned for the sake of clarity, it is to be understood that the functions of any combinations of the various units may be performed by a single hardware component within the one or more portable electronic devices, for example a microprocessor.

The portable processing component 701 may communicate with a sensing component 702 via a cable 703 or wireless communication to receive tracking data from the sensing component. In some embodiments, the tracking data may be transmitted from the portable sensing component to the processing component via a cable 703. In some embodiments, the tracking data may be transmitted from the sensing component to the portable processing component via wired internet, for example a wired local area network (LAN), and/or wireless communication, for example Global System for Mobile Communications (GSM), Enhanced Data GSM Environment (EDGE), Bluetooth, and Wireless Fidelity (Wi-Fi).

Figure 8:
FIG. 8 illustrates a single portable electronic device that functions as both a processing component and a sensing component in accordance with some embodiments.

FIG. 8 illustrates a subject 809 undergoing an examination using the disclosed screening systems and processes using a single smartphone 801 acting as both a portable processing component and sensing component. In some embodiments, the screening system 800, comprising a processing component and a sensing component, may be part of one electronic device. In the illustrated embodiment, for example, a smartphone 801 may be installed with a software program for executing the disclosed screening process, and the sensing component may be a gesture or eye-tracking component 802 of the smartphone 801. Thus, the subject 809 may undergo a dynamic motor tracking test by tracking a graphical image of the target 805 on the smartphone's display screen 804 using gestures or his/her eye movements. A graphical image of the tracker 806, representing the subject's tracking of the dynamic target 805 using his/her eye movements, is also depicted on the display screen 804 in real time.

FIG. 9 is a display screen 904 showing a graphical image of the target and a graphical image of the tracker during the course of a dynamic motor tracking task in accordance with some embodiments. In the illustrated embodiment, the target is a horizontal band 905 that moves up and down the display screen in an unpredictable pattern as instructed by the target generating unit. An unpredictable pattern represents an irregular, non-periodic, and non-repetitive movement such that the subject cannot predict in advance the target's future path. Thus, an unpredictable pattern tests a subject's feedback response. On the other hand, a predictable pattern, which represents a regular, periodic, and repetitive movement such that the subject can predict in advance the target's future path, tests a subject's feedforward response.

The target generating unit may implement, for example, an algorithm comprising a combination of one or more sine waves, cosine waves, and/or constants that produce an unpredictable movement pattern. For instance, the unpredictable algorithm may be similar in form to the following mathematical equation measuring force: $F(t)=\sin(2\pi f_1 t)+\sin(2\pi f_2 t)+\sin(2\pi f_3 t)+C$, where $f_1=0.2335$ Hz, $f_2=0.37$ Hz, $f_3=0.45$ Hz, and C is a constant that equals 5% of a subject's maximum grip-force, measured in Newtons, determined at the beginning of the motor tracking task. The frequencies $f_1$, $f_2$, and $f_3$ should be visually detectable by participants, and within a range that they can feasibly respond to (e.g., 0.1-10 Hz). A target mode based on this exemplary algorithm may generate an unpredictable movement pattern as represented graphically in FIG. 3A, which relates user-applied force to time. The target generating unit may also implement, for example, an algorithm comprising a single periodic sine and/or cosine wave, or a combination of one or more sine waves, cosine waves, and/or constants that produce a predictable movement pattern. For example, the algorithm may be one similar in form to the following mathematical equation: $F(t)=2\sin(2\pi ft)+C$, where $f=0.30$. The frequency f should be visually detectable by participants, and within a range that they can feasibly respond to (e.g., 0.1-10 Hz). A target mode based on this exemplary algorithm may generate a repetitive movement pattern as represented graphically in FIG. 3B, which relates user-applied force to time.

In the illustrated embodiment, the target is a horizontal band 905 and the subject-controlled tracker is a vertical band 906 located beneath the horizontal band 905. An operator, or a textual or audio message played by the processing component, may instruct the subject to "track" the dynamic target by controlling the vertical band. In the illustrated embodiment, "tracking" may comprise the subject attempting to keep the tip 906A of the vertical band 906 aligned with the bottom edge 905A of the horizontal band 905 over the course of the dynamic motor tracking task. For example, an increase in applied grip-force on the dynamometer may increase the height of the vertical band, and a decrease in applied grip-force may decrease the height of the vertical band. Accordingly, the subject may track the target by controlling the height of the vertical band using the dynamometer to heighten or shrink the vertical band in response to the up-and-down movements of the horizontal band. The change in height of the vertical band in response to changes in the subject's applied grip-force is shown on the display screen in real time; thus, the subject can constantly visualize his/her tracking actions and continuously attempt to make corrections when the bottom edge of the horizontal band moves out of line with the tip of the vertical band.

In some embodiments, the vertical band may instead move up and down in response to the subject's control. An increase in applied grip-force on the dynamometer may move the vertical band vertically upwards, and a decrease in applied grip-force may move the vertical band vertically downwards. Accordingly, the subject may attempt to keep the tip of the vertical band aligned with the bottom edge of the horizontal band by controlling the vertical position of the vertical band using the dynamometer.

It should be noted that the dynamic motor tracking task illustrated in FIG. 9 is only exemplary. The dynamic motor tracking task is not limited to the use of two moving or adjustable bands. In some embodiments, the target may be a differently-shaped dynamic graphical image, such as a circle or a square, which moves in one or more directions throughout the display screen in an unpredictable pattern as instructed by the target generating unit. In accord, the tracker may also be a differently-shaped graphical image that tracks the target via changes in size or position. In some embodiments, the target may be a dynamic line or point on a graph that moves in one or more directions throughout the display screen in an unpredictable pattern as instructed by the target generating unit. In accord, the tracker may also be a line or point on the graph. In some embodiments, the target may be a shape, for example a circle, triangle, rectangle, box, ball, or cylinder, which dynamically changes in size or volume. In accord, the tracker may also be a circle, triangle, rectangle, box, ball, cylinder, or the like, that tracks changes in size or volume of the target by expanding and contracting in response to changes in the subject's input.

The target generating unit may be capable of generating a plurality of different target modes. In some embodiments, the plurality of different target modes may appear on a menu screen or options screen such that it is easily selectable by an operator or user. In some embodiments, the target modes may be selectable by a physical button on the processing component. Each target mode may be programmed to generate instructions based on an algorithm most likely to maximize the accuracy of the final diagnosis depending on one or more characteristics of a potential subject. More specifically, each target mode may represent a unique algorithm tailored to a particular segment of a population, community, or entity. For example, a processing component used by the military may be programmed with one or more target modes representing unique algorithms tailored to military personnel. Similarly, a processing component used by a sports league, for instance the National Football League (NFL), may be programmed with one or more target modes representing unique algorithms tailored to professional football players. Further, each target mode may represent a unique algorithm tailored to a particular characteristic of a group. The characteristic may include, but is not limited to, gender, height, weight, and age group. For example, there may be separate target modes tailored to men of a certain age group or women of a certain age group.

Figure 10:
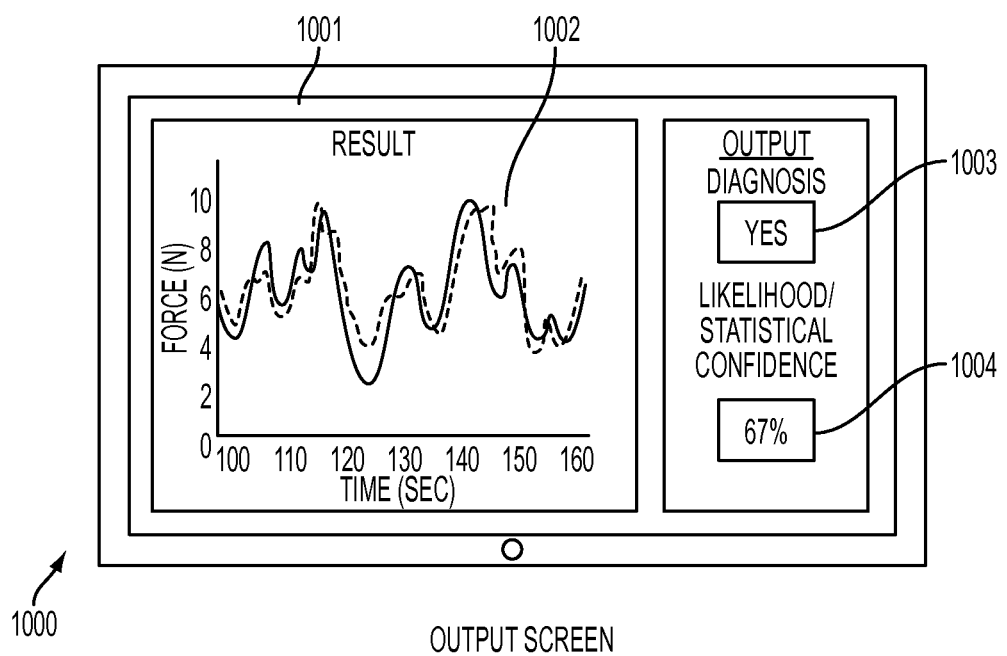
FIG. 10 is an exemplary output screen depicting a diagnosis for mTBI of a subject following the conclusion of a dynamic motor tracking task in accordance with some embodiments.

FIG. 10 is an output screen 100 indicating a diagnosis following the conclusion of a test in accordance with some embodiments. The display screen 101 depicts a screening indicator 103 that is indicative of the diagnosis. The diagnosis may be displayed in simple words, for example YES or NO, POSITIVE or NEGATIVE, or the like. In some embodiments, the diagnosis may additionally or alternatively be outputted via one or more light signals. For example, the screening indicator may show a red color for a positive diagnosis and a green color for a negative diagnosis. In some embodiments, the diagnosis may additionally or alternatively be outputted via audio. For example, the screening system may further include a speaker, which may play an audio message indicating the diagnosis.

The comparison unit may also generate a confidence interval which reflects the tracking data's support for the diagnosed classification. In such case, the output screen 100 may further include a statistical confidence value 104 based on the generated confidence interval. In some embodiments, the statistical confidence value may indicate the likelihood that the diagnosis is correct. In some embodiments, the statistical confidence value may indicate the likelihood that the subject has or does not have mTBI, irrespective of the diagnosis. In some embodiments, the statistical confidence value 104 may be an interval ranging between two percentages.

In some embodiments, the comparison unit may further apply the confidence interval to reduce false negative diagnoses. For example, the comparison unit may be biased to produce negative classifications only when the particular negative classification is highly confident based on the confidence interval, thereby reducing the likelihood of generating false negatives.

In some embodiments, if the confidence value is below a certain threshold, for example below 70%, the comparison unit may cause the screening system to output a request to re-take the motor tracking examination. In some embodiments, if the confidence value is below a certain threshold, for example below 70%, and the subject has already been tested at least a pre-determined number of times, for example at least three times, the comparison unit may cause the screening system to output a request to seek a clinical diagnosis.

In addition to tracking data gathered via the dynamic motor tracking task, the comparison unit may further incorporate other subject-specific data that may be available from the subject's previous screening tests or conventional evaluative measurement scores.

In some embodiments, the comparison unit may incorporate baseline motor response data of the subject as an additional barometer to compare to the subject's current performance. Further, the screening system may be used, without modification, to gather individual baseline motor response data. Baseline motor response data may be representative tracking data of a subject obtained using the screening system at a time when the subject has not been exposed to a traumatic incident. Different individuals may, even when fully healthy, vary wildly in terms of inherent motor tracking ability. For example, trained athletes may possess stronger inherent motor skills compared to a typical non-athlete. Thus, it may be the case that a trained athlete may perform better on a motor tracking task, even if concussed, than a non-athlete may perform on the same motor tracking task, even when not concussed. Therefore, it may improve the reliability of the screen system if the comparison system incorporates baseline motor response data in order to account for inherent differences in motor skills among individuals.

In some embodiments, the comparison unit may incorporate subject-specific conventional mTBI evaluative scores and measurements. For example, the processing component may incorporate additional relevant measurements from conventional mTBI evaluation sources in addition to the tracking data to determine a diagnosis. This may include test scores from standard mTBI questionnaires, including but not limited to the Military Acute Concussion Evaluation (MACE), the Westmead Post Traumatic Amnesia Scale (PTA), and the Acute Concussion Evaluation (ACE). If conventional measurements are incorporated into the screening analysis, the output screen may depict two different screening indicators, one incorporating the subject's conventional data and the other ignoring the subject's conventional data.

In order to retrieve subject-specific third-party evaluation scores, the screening system may have access to a database containing a collection of user profiles of known subjects from where it can retrieve the subject's evaluation history. In some embodiments, the user-profile database may be contained in one or more non-volatile memories that comprise a part of the processing component, for example a hard disk drive (HDD) or a solid-state drive (SSD). In some embodiments, the user-profile database may be contained in a portable data storage device, for example a Universal Serial Bus (USB) flash drive or a Secure Digital (SD) memory card. In some embodiments, the user-profile database may be contained in one or more online servers, for example servers hosted at a centralized location. The processing component may then access the user-profile database stored in one or more online servers via wired internet, for example a wired local area network (LAN), and/or wireless communication, for example Wireless Fidelity (WiFi) and mobile telecommunications technology such as Long-Term Evolution (LTE).

The output screen 100 may also depict on the display screen 101 a plot 102 demonstrating the performance of the subject in graphical form. For example, the plot may convey the result of a completed grip-force dynamometry task, based on an unpredictable pattern mode, in terms of force (N) as a function of time (seconds). A solid line may represent the movement of the target in terms of force over time, and a dotted line may represent the movement of the tracker in terms of force over time. The plot may be generated from the tracking data received from the sensing component, and the target data received from the target generating unit.

Figure 11:
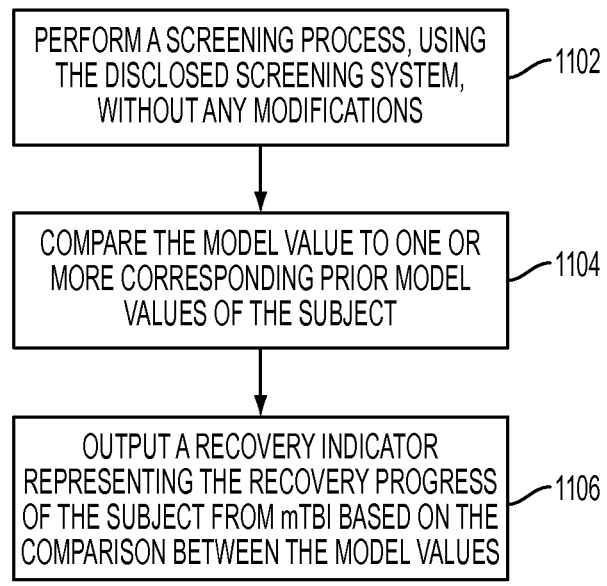
FIG. 11 is a flow diagram illustrating a process for determining a progress of recovery from a brain injury in accordance with some embodiments.

FIG. 11 is a flow diagram illustrating a recovery screening process in accordance with some embodiments. At step 1102, the recovery screening process is performed using the disclosed screening system and process, without any modifications, by a subject who has already been diagnosed using the screening system at least one previous time prior to the current examination. Accordingly, there may be one or more prior model values from previous tests belonging to the particular subject stored in a database.

At step 1104, a model value generated from a present screening process is compared to the prior one or more corresponding model values belonging to the same subject retrieved from the database. In some embodiments, a change in numerical value of the same model parameter over two or more tests at different points in time may be indicative of a progressing recovery from mTBI. For example, the numerical value of a model parameter may decrease over subsequent tests. If the decrease is exponential, the decrease may be deemed significant.

In some embodiments, a particular model parameter may be particularly sensitive to recovery relative to the other model parameters. For example, because the numerical values for the model parameters $K_p$, $K_d$, and $\tau$ generated by a parameter generating unit implementing the exemplary feedback response model described above with respect to FIG. 1 are sensitive to mTBI, their numerical values for the same subject may change as the condition of the subject's injury improves or deteriorates. In particular, the differential parameter $K_d$ may decrease exponentially over time since the time of injury as the subject recovers from mTBI. A substantial decrease in the numerical value of a model parameter over time, such as an exponential decrease, may be indicative of progressing recovery from mTBI. On the other hand, a substantial increase in the numerical value of a model parameter over time, such as an exponential increase, may be indicative of worsening of mTBI.

At step 1106, the processing component may output, in addition to or alternatively to outputting the screening indicator, a recovery indicator representing the recovery progress of the subject based on the comparison between one or more present and prior corresponding model values. In some embodiments, the processing component may further output information regarding which particular model parameter was most relevant to the recovery diagnosis. For a screening process implementing the exemplary feedback response model with model parameters $K_p$, $K_d$, and $\tau$, the differential parameter $K_d$ may be most relevant based on its exponential decrease over time. In some embodiments, the processing component may further output an estimated recovery time to full recovery. For example, the comparison unit may determine that a certain amount of decrease in one or more of the subject's model values will result in a re-classification of the subject from mTBI-positive to mTBI-negative. The comparison unit may then estimate an approximate time that will need to pass before the relevant model value(s) crosses this threshold based on the subject's prior testing history and recovery progress results.

FIG. 12 is a table comparing classification results from the exemplary feedback response model, discussed above with respect to FIG. 1, to other publicly available evaluation methods with the same twenty-nine test participants. The twenty-nine test participants comprise fourteen non-mTBI controls and fifteen mTBI patients. The exemplary feedback response model, using $K_p$, $K_d$ and $\tau$, is tested to have a predictive accuracy of 89.7% using a leave-one-out cross-validation method over test participants. By contrast, both the MACE test and the Physicians' Health Questionnaire (PHQ-9) shows a predictive accuracy of 72.4% based on the same twenty-nine test participants. Classification via Trails Making Test A is significantly less accurate (p=0.024), at 55.2% based on same twenty-nine test participants. Simpler metrics such as the standard deviation of the tracking error (STDEV) and $\tau$ (lag) is also less accurate (p=0.041), at 69.0% based on the same twenty-nine test participants.

Figure 13:
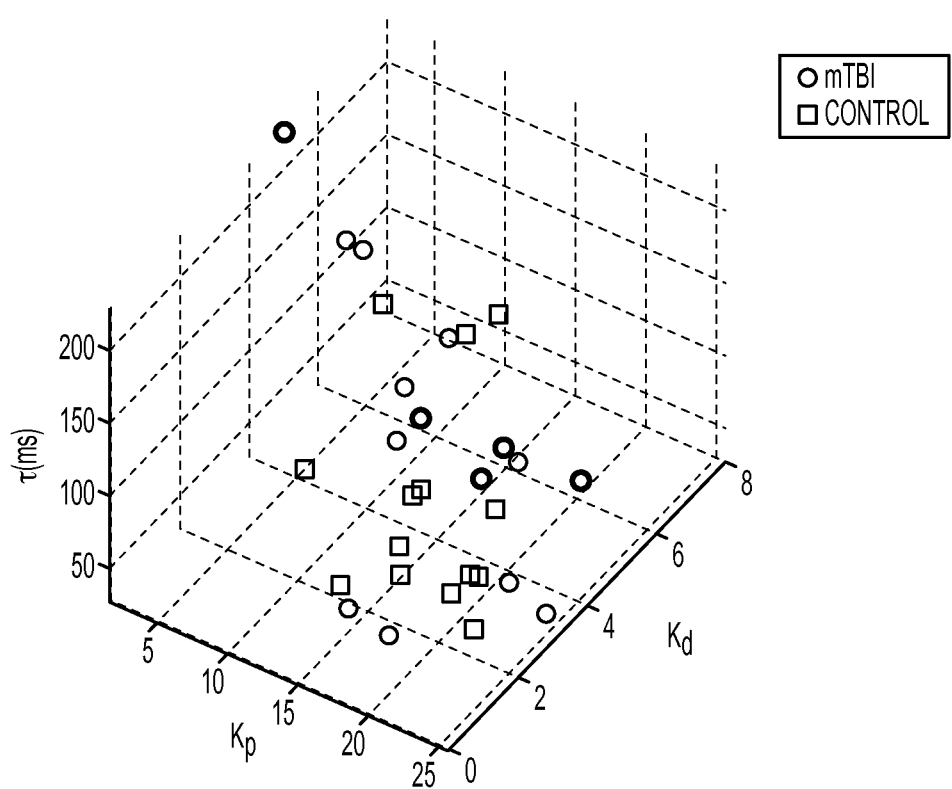
FIG. 13 is a graphical illustration of several data points representing numerical values for model parameters of different individuals generated by an exemplary feedback response model in accordance with some embodiments.

FIG. 13 is a three dimensional graph illustrating the comparison unit, for example a machine learning predictor, implementing a Gaussian Process classifier to three model parameters $K_p$, $K_d$ and $\tau$ generated from the exemplary feedback response model discussed with respect to FIG. 1 in accordance with some embodiments. The response graph depicts a cluster of circle data points representing mTBI patients and a cluster of square data points representing non-mTBI controls. A feedback response model and machine learning predictor that generate a response graph depicting data points that are more tightly-clustered may represent a screening process with a higher degree of accuracy. Further, a data point of a particular response graph that is further displaced from the center point of a data cluster may represent a data point with a diagnosis having a lower statistical confidence value. Analogously, a data point of a particular response graph that is closely placed to the center point of a data cluster may represent a data point with a diagnosis having a higher statistical confidence value.

In some embodiments, the comparison unit may combine the model values quantified from the dynamic motor tracking task with other behavioral tests from third-party evaluative sources. A combination of the disclosed dynamic motor tracking task with other available tests may further enhance the accuracy of the diagnosis. Possible complimentary behavioral tests include but are not limited to the Automated Neuropsychological Assessment Test (ANAM), the Immediate Post-Concussion Assessment and Cognitive Testing (ImPACT), and the King-Devick (K-D) Test.

The invention claimed is:

1. A method for screening a brain injury using one or more electronic devices comprising:
   displaying an image of a dynamic target on a display for a subject to track using a sensing component;
   receiving, from the sensing component, tracking data representing the subject's tracking of the dynamic target;
   displaying in real time an image of a tracker on the display representing the subject's tracking of the dynamic target;

determining a model value, derived from target data and the tracking data, indicative of the subject's corrective actions in response to deviations between the tracker and the dynamic target over a period of time;

comparing the model value to one or more multi-subject model values; and outputting a screening indicator representing a likelihood that the subject has a brain injury based on the compared model values.

2. The method of claim 1, further comprising:

comparing the model value to a corresponding prior model value of the subject; and outputting a prior screening indicator representing a recovery progress of the subject from a brain injury based on the comparison between the model values.

3. The method of claim 2, wherein the prior screening indicator comprises a screening indicator of the subject from a threshold amount of time prior to the current time.

4. The method of claim 1, wherein the brain injury is a mild traumatic brain injury.

5. The method of claim 1, wherein the one or more electronic devices comprise one or more portable devices.

6. The method of claim 1, wherein the dynamic target moves in accordance with one or more of a plurality of target modes, and each of the target modes instructs the dynamic target to move in a unique pattern.

7. The method of claim 1, wherein the sensing component is a dynamometer that detects the subject's hand grip force.

8. The method of claim 1, wherein the sensing component is an eye-tracking device.

9. The method of claim 1, wherein the tracker is an icon on the display that expands and contracts in response to the subject's input using the sensing component.

10. The method of claim 1, wherein the model value is derived from the tracking data via a response model that correlates the deviations between the tracker and the dynamic target to the subject's corrective actions over a period of time.

11. The method of claim 10, wherein the model value comprises one or more best-fit parameters representing optimized fit values quantified by the response model using the tracking data.

12. The method of claim 1, wherein the one or more multi-subject model values comprise one or more model values of previously tested subjects.

13. The method of claim 12, wherein the previously tested subjects comprise individuals known to have a brain injury and individuals known not to have a brain injury.

14. The method of claim 13, wherein the previously tested subjects comprise individuals having two or more of gender, height, weight, and age group in common with the subject.

15. The method of claim 14, wherein the previously tested subjects comprise individuals employed in the same field of employment as the subject.

16. The method of claim 1, wherein comparing the model value to the one or more multi-subject model values comprises implementing a machine learning predictor that uses a Gaussian process.

17. The method of claim 16, comprising comparing a plurality of assessment scores of the subject to a plurality of assessment scores of multiple subjects from the multi-subject model.

18. The method of claim 17, wherein the plurality of assessment scores of the multiple subjects comprise evaluative scores from post-concussion questionnaires.

19. The method of claim 1, wherein outputting the screening indicator comprises displaying at least one of a light in one or more colors, an audio signal or text.

* * * * *